United States Patent
Wales et al.

(10) Patent No.: US 9,277,914 B2
(45) Date of Patent: *Mar. 8, 2016

(54) TISSUE FIXATION DELIVERY APPARATUS

(71) Applicant: BOSTON SCIENTIFIC NEUROMODULATION CORPORATION, Valencia, CA (US)

(72) Inventors: Lawrence W. Wales, Maplewood, MN (US); Ishmael Bentley, Eagan, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,151

(22) Filed: Apr. 24, 2015

(65) Prior Publication Data

US 2015/0230789 A1    Aug. 20, 2015

Related U.S. Application Data

(63) Continuation of application No. 14/024,259, filed on Sep. 11, 2013, now Pat. No. 9,039,740.

(60) Provisional application No. 61/704,009, filed on Sep. 21, 2012.

(51) Int. Cl.
*A61B 17/04* (2006.01)

(52) U.S. Cl.
CPC ..... *A61B 17/0401* (2013.01); *A61B 2017/0409* (2013.01); *A61B 2017/0464* (2013.01)

(58) Field of Classification Search
CPC .......... A61B 17/0401; A61B 17/105; A61B 2017/00473; A61B 2017/00477; A61B 2017/0409; A61B 2017/0417; A61B 2017/0464

USPC ....... 221/312 A; 446/472, 473, 483; 606/104, 606/143, 144, 147, 151, 232; 623/13.14
See application file for complete search history.

(56) References Cited

U.S. PATENT DOCUMENTS

| | | | |
|---|---|---|---|
| 4,821,721 A * | 4/1989 | Chin et al. | 606/143 |
| 2007/0100348 A1 | 5/2007 | Cauthen et al. | |
| 2009/0112232 A1* | 4/2009 | Crainich et al. | 606/139 |
| 2011/0082472 A1 | 4/2011 | Harris et al. | |
| 2011/0172682 A1* | 7/2011 | Brady et al. | 606/144 |
| 2012/0143215 A1 | 6/2012 | Corrao et al. | |

OTHER PUBLICATIONS

International Search Report and Written Opinion for PCT/US2013/059259 mailed Jan. 23, 2014.

* cited by examiner

*Primary Examiner* — Todd E Manahan
*Assistant Examiner* — Charles Wei
(74) *Attorney, Agent, or Firm* — Lowe Graham Jones PLLC; Bruce E. Black

(57) ABSTRACT

A device for deploying a tissue fixation apparatus of the type including first and second tissue anchors coupled together by an adjustable suture assembly. The device comprises a handle mechanism and a needle cartridge assembly releasably coupled to the handle mechanism. The needle cartridge assembly includes a needle cannula with a side opening through which a tissue anchor can be loaded into an internal chamber of the needle cannula. A push rod is disposed in the needle cannula and is operable between an extended position in which the push rod prevents the tissue anchor from entering the chamber through the side opening, and a retracted configuration in which the tissue anchor can be pushed into the chamber under the action of a resilient band positioned over the side opening.

20 Claims, 7 Drawing Sheets

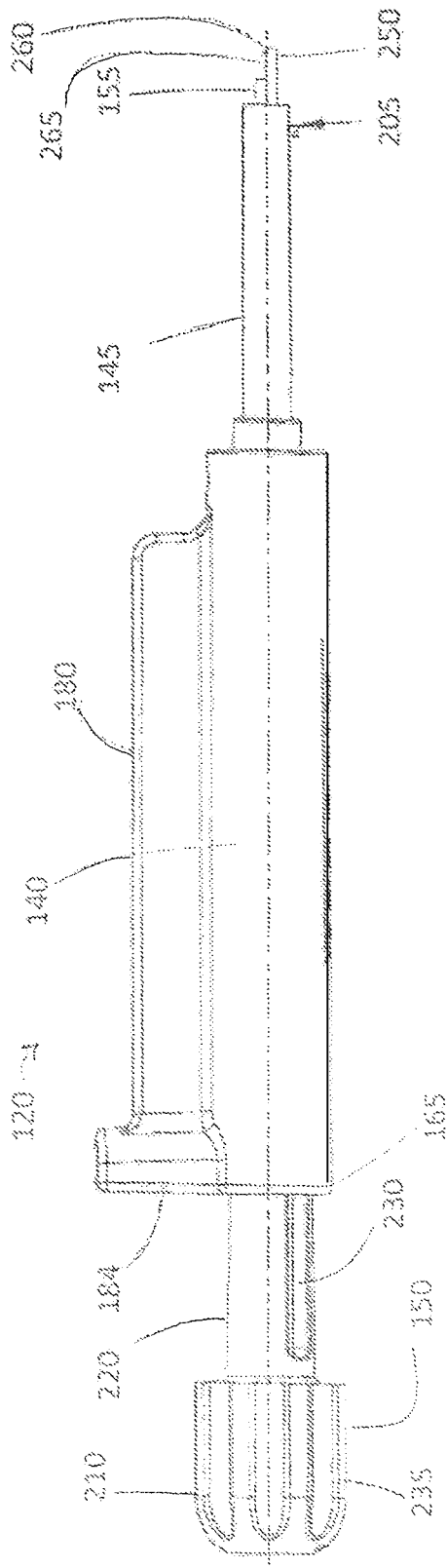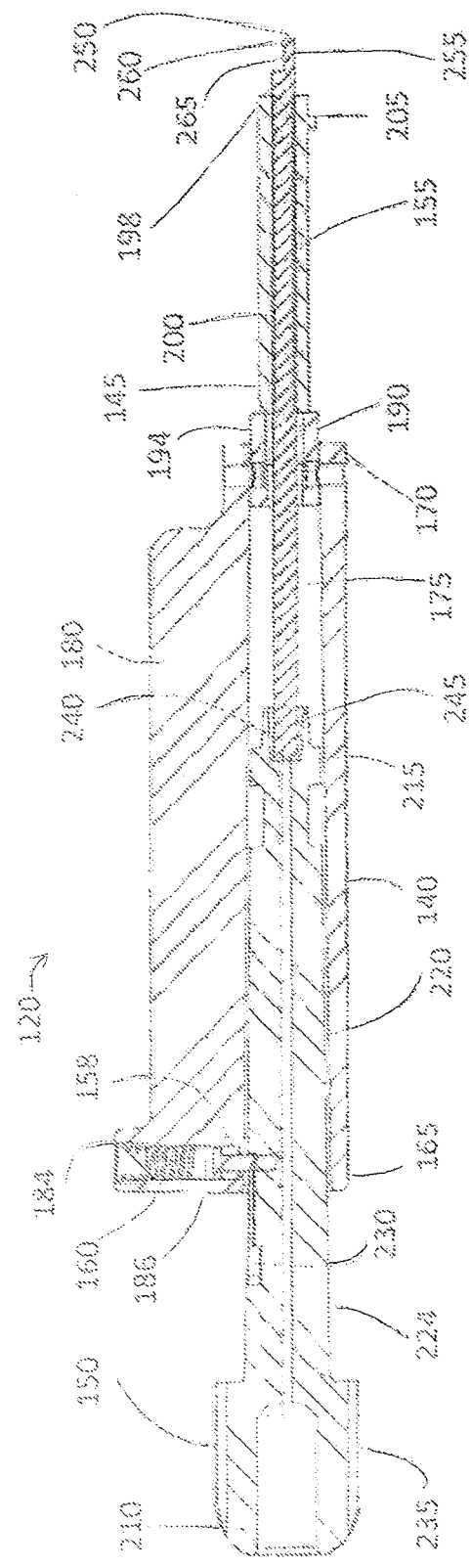

TISSUE FIXATION DELIVERY APPARATUS

CROSS-REFERENCE TO RELATED APPLICATIONS

This application is a continuation of U.S. patent application Ser. No. 14/024,259 filed Sep. 11, 2013 which claims the benefit under 35 U.S.C. §119(e) of U.S. Provisional Patent Application Ser. No. 61/704,009 filed Sep. 21, 2012, both of which are incorporated herein by reference.

TECHNICAL FIELD

The present invention relates to medical devices and methods for tissue anchoring and fixation. More specifically, the invention relates to devices and methods for deploying tissue anchors into soft tissues of the body.

BACKGROUND

Various medical procedures benefit from the use of tissue fixation devices for repairing damaged tissues and/or for securing other devices to the patient. Exemplary tissue fixation devices can include one or more tissue and/or bone anchors coupled to one or more suture elements. The particular configuration of the anchor/suture constructs can vary from procedure to procedure. There is a continuing need for improved devices and methods for deploying such tissue fixation devices in an efficient manner.

SUMMARY

In Example 1, the present invention is a device for deploying a tissue fixation apparatus of the type including first and second tissue anchors coupled together by an adjustable suture assembly. The device comprises a handle mechanism and a needle cartridge assembly releasably coupled to the handle mechanism. The handle mechanism includes a handle body, a tubular shaft, a plunger, and a handle push rod. The handle body has a proximal end and a distal end and an internal cavity disposed therebetween. The tubular shaft extends distally from the handle body and having a distal end. The plunger is slidably and rotatably coupled to the body and has a proximal end and a distal end, the proximal end positioned external to and proximal to the handle body, the distal end positioned within the internal cavity of the body. The handle push rod extends distally from the plunger and is slidably and rotatably disposed within the tubular shaft, and includes a distal mating feature. The needle cartridge assembly includes a needle cannula, a tubular sleeve, a cartridge push rod, and a resilient band. The needle cannula has an outer wall defining a proximal portion, an opposite sharpened distal tip having a distal opening, an internal chamber extending from the proximal portion through the distal opening, and a needle side opening through the outer wall. The tubular sleeve is fixedly disposed about a portion of the needle cannula and has a proximal end and a distal end, the proximal end of the tubular sleeve configured to mate with the distal end of the tubular shaft of the handle mechanism for coupling the handle mechanism and the needle cartridge assembly. The tubular sleeve further includes a sleeve side opening radially and axially aligned with the needle side opening. The cartridge push rod is slidably and rotatably disposed within the chamber of the needle cannula and includes a proximal mating feature configured to engage the distal mating feature of the handle push rod. The resilient band is disposed about disposed the tubular sleeve within the groove and over the side opening. Prior to deployment the first tissue anchor is disposed within the internal chamber of the needle cannula and the second tissue anchor is disposed external to the internal chamber within the side opening in the sleeve, and wherein the plunger, the handle push rod and the cartridge push rod are positioned such that the cartridge push rod operates to prevent the second tissue anchor from entering the internal chamber while the resilient band operates to urge the second tissue anchor toward the internal chamber.

In Example 2, the device of Example 1, wherein the plunger and the handle and cartridge push rods are configured to operate between at least one extended position and at least one retracted position, wherein in the at least one extended position the cartridge push rod is located so as to eject the first tissue anchor from the chamber through the distal opening of the needle cannula while preventing the second tissue anchor from entering the internal chamber, and wherein in the at least one retracted position the cartridge push rod is positioned proximal to the side opening in the sleeve so as to allow the second tissue anchor to be urged into the internal chamber through the needle side opening by the resilient band.

In Example 3, the device of Example 2, wherein the plunger and the handle and cartridge push rods are further configured to be operable to eject the second tissue anchor from the internal chamber through the distal opening of the needle cannula.

In Example 4, the device of any of Examples 1-3, wherein the proximal end of the tubular sleeve includes a proximal opening configured to receive the distal end of the tubular shaft of the handle mechanism so as to couple the handle mechanism to the needle cartridge assembly.

In Example 5, the device of Example 4, wherein the distal end of the tubular shaft and the proximal opening of the tubular sleeve are sized to form an interference fit therebetween to couple the handle mechanism to the needle cartridge assembly.

In Example 6, the device of any of Examples 1-5, wherein the distal end of the tubular shaft includes an alignment pin extending radially outward therefrom, and wherein the proximal end of the tubular sleeve includes a notch sized to receive the alignment pin to radially align the handle mechanism and the needle cartridge.

In Example 7, the device of any of Examples 1-6, wherein the handle mechanism and the needle cartridge assembly are releasably couple to one another in such a way that, upon relative separation thereof, the distal mating feature of the handle push rod and the proximal mating feature of the cartridge push rod are configured to disengage one another.

In Example 8, the device of any of Examples 1-7, wherein the plunger has an intermediate section including an outer surface and a groove arrangement therein, and wherein the handle mechanism further includes a guide pin extending radially inward, the guide pin being spring biased toward the plunger so as to extend partially within the groove arrangement to regulate longitudinal and rotational movement of the plunger relative to the handle body.

In Example 9, the device of any of Examples 1-8, wherein prior to complete deployment of the tissue fixation apparatus a portion of the suture assembly is releasably coupled to the handle mechanism.

In Example 10, the device of any of Examples 1-9, wherein the tubular sleeve and the needle cannula each further include a slot extending from the distal end thereof to the side opening thereof, the tubular sleeve slot being radially aligned with the slot in the needle cannula.

In Example 11, the device of Example 10, wherein the slots of the tubular sleeve and the needle cannula are sized to receive at least a portion of the adjustable suture assembly of the tissue fixation apparatus.

In Example 12, a method of deploying a tissue fixation apparatus of the type including first and second tissue anchors coupled together by an adjustable suture assembly, the tissue fixation apparatus being pre-loaded onto a delivery tool with the first tissue anchor disposed within an interior chamber of a needle cannula of the delivery tool. The method comprises inserting a sharpened distal tip of the needle cannula into target tissue at a first location, and then advancing a push rod distally within the needle cannula to eject the first tissue anchor from the needle cannula within the target tissue at the first location. The method further comprises then withdrawing the needle cannula from the first location and inserting the sharpened distal tip into the target tissue at a second location, and withdrawing the push rod with respect to the needle cannula to allow the second tissue anchor to be pushed into the interior chamber of the needle cannula under the operation of a resilient band disposed about the needle cannula and the second tissue anchor. The method further comprises next advancing the push rod distally within the needle cannula to eject the second tissue anchor from the needle cannula within the target tissue at the second location, and then withdrawing the needle cannula from the tissue and tightening the tissue fixation apparatus.

In Example 13, the method of Example 12, wherein the delivery tool includes a handle mechanism and a needle cartridge assembly including the needle cannula, and wherein the tissue fixation apparatus is preloaded onto the needle cartridge assembly, and wherein the method further comprises coupling the handle mechanism and the needle cartridge assembly together prior to inserting the sharpened distal tip of the needle cannula into the target tissue.

In Example 14, the method of any of Examples 12-13, further comprising decoupling the needle cartridge assembly and the handle mechanism after withdrawing the needle cannula from the target tissue.

In Example 15, the method of any of Examples 12-14, wherein coupling the handle mechanism and the needle cartridge assembly together includes inserting a tubular shaft of the handle mechanism into a proximal opening of the needle cartridge assembly.

Example 16 is a tissue fixation system comprising a handle mechanism and a kit including a needle cartridge assembly and a tissue fixation apparatus coupled thereto. The handle mechanism includes a handle body, a tubular shaft, a plunger and a handle push rod. The handle body has a proximal end and a distal end and an internal cavity disposed therebetween. The tubular shaft extends distally from the handle body and having a distal end. The plunger is slidably and rotatably coupled to the body and has a proximal end and a distal end, the proximal end positioned external to and proximal to the handle body, the distal end positioned within the internal cavity of the body. The handle push rod extends distally from the plunger and is slidably and rotatably disposed within the tubular shaft, the handle push rod including a distal mating feature. The needle cartridge assembly includes an elongate needle cannula, a tubular sleeve, a cartridge push rod, and a resilient band. The needle cannula has an outer wall defining a proximal portion, an opposite sharpened distal tip having a distal opening, an internal chamber extending from the proximal portion through the distal opening, and a needle side opening through the outer wall. The tubular sleeve is fixedly disposed about a portion of the needle cannula having a proximal end and a distal end, the proximal end of the tubular sleeve configured to mate with the distal end of the tubular shaft of the handle mechanism for coupling the handle mechanism and the needle cartridge assembly. The tubular sleeve further includes a sleeve side opening radially and axially aligned with the needle side opening. The cartridge push rod is slidably and rotatably disposed within the internal chamber of the needle cannula and includes a proximal mating feature configured to engage the distal mating feature of the handle push rod. The resilient band is disposed about disposed the tubular sleeve within the groove and over the side opening. The tissue fixation apparatus includes a first tissue anchor, a second tissue anchor, and an adjustable suture assembly coupling the first and second tissue anchors together. The adjustable suture assembly includes an adjustable suture loop and a tension line, wherein the first and second tissue anchors are coupled to the adjustable suture loop, and wherein the tension line is operable to reduce a dimension of the adjustable suture loop between the first and second tissue anchors. The first tissue anchor is disposed within the internal chamber of the needle cannula, the second tissue is disposed external to the internal chamber and within the needle and sleeve side openings, and the resilient band is disposed about the tubular sleeve over the second tissue anchor so as to urge the second tissue anchor toward the internal chamber through the needle and sleeve side openings. The cartridge push rod is positioned so as to prevent the second tissue anchor from entering the internal chamber. Upon coupling the tubular shaft of the handle mechanism and the tubular sleeve of the needle cartridge assembly together, and further wherein upon coupling the mating features of the handle and needle push rods together, the plunger and the handle and cartridge push rods are configured to operate between at least one extended position and at least one retracted position. In the at least one extended position the cartridge push rod is located so as to eject the first tissue anchor from the internal chamber through the distal opening of the needle cannula while preventing the second tissue anchor from entering the internal chamber. In the at least one retracted position the cartridge push rod is positioned proximal to the side opening in the sleeve so as to allow the second tissue anchor to be urged into the internal chamber through the needle side opening by the resilient band.

In Example 17, the tissue fixation system of Example 16, wherein the proximal end of the tubular sleeve includes a proximal opening configured to receive the distal end of the tubular shaft of the handle mechanism so as to couple the handle mechanism to the needle cartridge assembly.

In Example 18, the tissue fixation system of either of Examples 16 or 17, wherein the distal end of the tubular shaft and the proximal opening of the tubular sleeve are sized to form an interference fit therebetween to couple the handle mechanism to the needle cartridge assembly.

In Example 19, the tissue fixation system of either of any of Examples 16-18, wherein the distal end of the tubular shaft includes an alignment pin extending radially outward therefrom, and wherein the proximal end of the tubular sleeve includes a notch sized to receive the alignment pin to radially align the handle mechanism and the needle cartridge assembly.

In Example 20, the tissue fixation system of any of Examples 16-19, wherein the tubular sleeve and the needle cannula each further includes a slot extending from the distal end thereof to the side opening thereof, the tubular sleeve slot being radially aligned with the slot in the needle cannula, and wherein the slots of the tubular sleeve and the needle cannula are sized to receive at least a portion of the adjustable suture assembly of the tissue fixation apparatus.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 2A and 2B are, respectively, elevation and cross-sectional elevation views of a handle mechanism portion of the delivery tool of the tissue fixation system of FIG. 1 according to one embodiment.

Figure 1A:
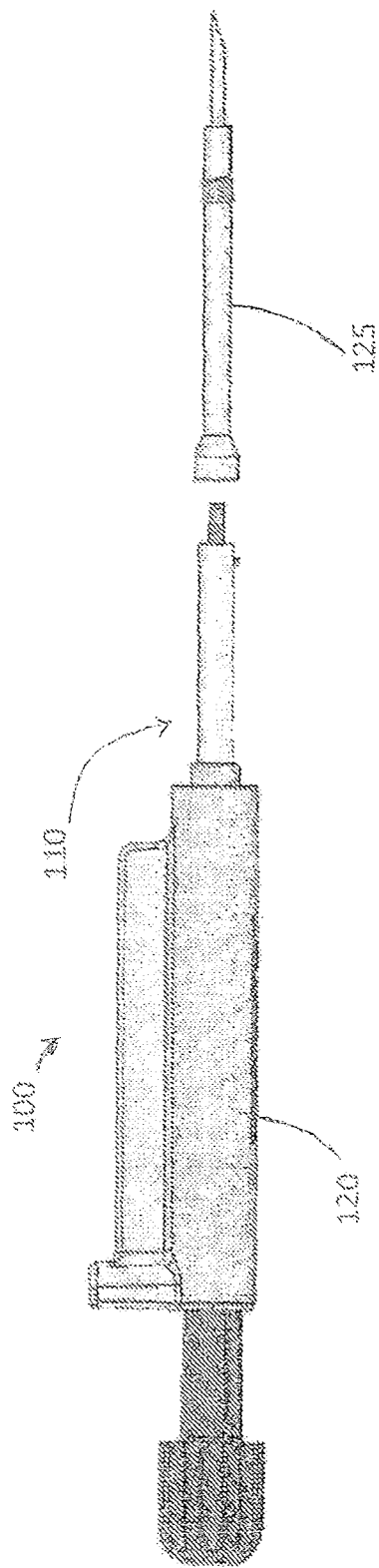
FIGS. 1A and 1B are side elevation views of a tissue fixation system including a delivery tool and a tissue fixation apparatus according to one embodiment of the present invention.

While the invention is amenable to various modifications and alternative forms. specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1B:
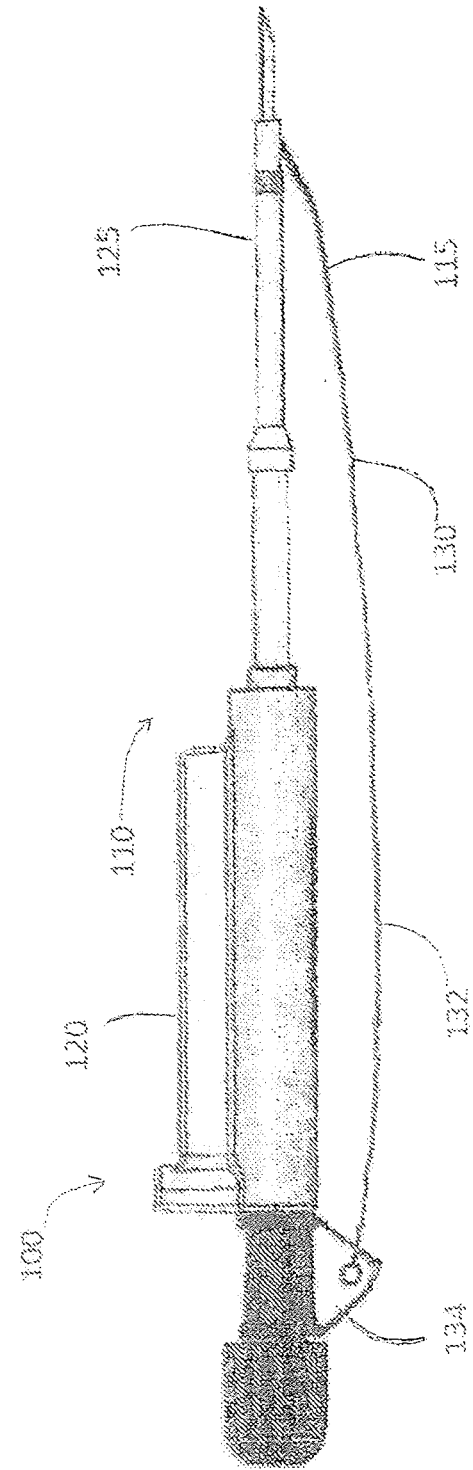

FIG. 1A is a side elevation view of a tissue fixation system 100 including a delivery tool 110 and a tissue fixation apparatus 115 coupled thereto according to one embodiment of the present invention. As shown in FIG. 1, the delivery tool 110 includes a handle mechanism 120 and a needle cartridge assembly 125 coupled thereto. In various embodiments, the handle mechanism 120 and the needle cartridge assembly 125 are releasably coupled to one another to permit separation of the needle cartridge assembly 125 after deployment of the tissue fixation apparatus 115. FIG. 1B is a side elevation view of the delivery tool 110 showing the needle cartridge assembly 125 separated from the handle mechanism 120. This separable design advantageously allows, for example, multiple tissue fixation apparatuses 115 to be utilized where required for a given medical procedure, while still allowing the handle mechanism 120 of the delivery tool 110 to be reused if desired by the clinician.

As further shown, the tissue fixation apparatus 115 includes a suture assembly 130, a portion of which (i.e., a tension line 132) is shown in FIG. 1A extending from the needle cartridge assembly 125 to a tab 134 coupled to a portion of the handle mechanism 120. In the various embodiments, the tissue fixation apparatus can take on various configurations tailored for the particular medical procedure being performed. In various embodiments, the tissue fixation apparatus includes a pair of tissue anchors (not shown in FIG. 1A) coupled together by the adjustable suture assembly 130 (e.g., via an adjustable suture loop), which can be tightened by applying tension to the tension line 132 after the tissue anchors are deployed into and secured within the target tissue.

Exemplary tissue fixation apparatuses that are contemplated within the scope of the various embodiments include, without limitation, those described in co-pending and commonly-assigned U.S. Patent Application Publication No. 2007/0100348, the contents of which are incorporated herein by reference in its entirety. As explained in further detail herein, in various embodiments, the tissue fixation apparatus 115 can be simplified from those disclosed in, for example, the aforementioned U.S. Patent Application Publication No. 2007/0100348 due to the design of the delivery tool 110, which can eliminate the need for a separate suture retention line coupled to the delivery tool for preventing unintended deployment of one of the tissue anchors as the tool is manipulated by the clinician. In various embodiments, the tissue fixation system 100 can be particularly useful for a variety of medical procedures, including without limitation, orthopedic procedures in the spine (e.g., re-approximation of defects or tears of the annulus fibrosus), the knee (e.g., meniscal repair procedures), or the extremities. In various embodiments, the tissue fixation system 100 can be useful for securing other medical devices (e.g., stimulation electrodes, catheters, and the like) to body tissues.

As explained previously, and as can be seen in FIGS. 1A and 1B, the handle mechanism 120 and the needle cartridge assembly 125 are releasably coupled to one another to permit separation of the needle cartridge assembly 125 after deployment of the tissue fixation apparatus 115. In such embodiments, multiple needle cartridge assemblies 125 can be provided each pre-loaded with the tissue fixation apparatus 115. Upon deployment of a first tissue fixation apparatus 115, the needle cartridge assembly 125 can be detached from the handle mechanism 120, as shown in FIG. 1B, and a second needle cartridge assembly 125 with the tissue fixation apparatus 115 pre-loaded thereon can be attached to the handle mechanism 120 (which can include releasably securing the tab 134 to the handle mechanism 120 as shown in FIG. 1A). In various embodiments, various kits including a range of needle cartridge assemblies 125 and tissue fixation apparatuses 115 (e.g., with different tissue anchor/suture constructs) can be provided to meet the particular needs of the various stages of the medical procedure being performed.

FIGS. 2A and 2B are, respectively, elevation and cross-sectional elevation views of the handle mechanism 120 of the delivery tool 110 according to one embodiment. As shown in FIGS. 2A and 2B, the handle mechanism 120 includes, in the illustrated embodiment, a handle body 140, a tubular shaft 145, a plunger 150, a handle push rod 155, a guide pin 158 and a spring 160. In the various embodiments, the handle mechanism 120 provides a means by which the clinician can manipulate and operate the various features of the delivery tool 110, as will be explained in further detail herein.

As further shown, the handle body 140 has a proximal end 165, an opposite distal end 170, an internal cavity 175, an external flange 180, and a post 184 defining a spring retaining channel 186. In one embodiment, the external flange 180 is relatively flat and extends along a longitudinal length of one side of the handle body 140, and provides a means by which a clinician can grasp the handle mechanism 120 during use of the delivery tool 110. As further shown, the internal cavity 175 extends generally longitudinally within the handle body 140, while the post 184 and the spring retaining channel 186 extend generally orthogonal to the longitudinal axis of the delivery tool 110 near the proximal end 165 of the body 140.

In the illustrated embodiment, the tubular shaft 145 includes a proximal end 190, which in the particular embodiment includes a collar 194, an opposite distal end 198, a longitudinal channel 200 and an alignment pin 205. As shown, tubular shaft 145 is fixedly coupled to and extends distally from the distal end 170 of the handle body 140, and the collar 194 is an enlarged diameter portion of the proximal end 190 and operates to couple the tubular shaft 145 to the handle body 140. In various embodiments, the collar 194 can be omitted, and the tubular shaft 145 can be coupled to the handle body 140 by other means, or in some embodiments, can be integrally formed with the handle body 140.

As further shown in FIGS. 2A and 2B, the plunger 150 includes a proximal end 210, an opposite distal end 215, and an intermediate section 220 therebetween defining an outer surface 224 of the plunger 150. Additionally, in the illustrated embodiment, the plunger 150 includes a groove arrangement 230 extending longitudinally and circumferentially along the outer surface 224 of the intermediate section 220. Still additionally, the plunger 150 includes a control knob 235 at the proximal end 210, and a distal recess 240 at the distal end 215.

In the illustrated embodiment, the handle push rod 155 has a proximal end 245 and an opposite distal end 250. As further shown, the distal end 250 includes a distal mating feature 255 including an inwardly extending tooth 260 and a generally flat face 265 extending proximally with respect to the tooth 260. In the illustrated embodiment, the majority of the handle push rod 155 (not including the distal mating feature 255) has a generally round cross-sectional profile, and can be solid or tubular. In other embodiments, other cross-sectional profiles (e.g., rectangular, polygonal, elliptical, and the like) can be utilized for this portion of the handle push rod 155.

As can be seen in FIGS. 2A and 2B, the proximal end 245 of the handle push rod 155 is received within the distal recess 240 of the plunger 150 and is fixedly coupled to the plunger 150 therein by any attachment means. Additionally, the plunger 150 is partially disposed within the internal cavity 175 of the handle body 140, with the proximal end 210 and part of the intermediate section 220 of the plunger 140 disposed external and proximal to the handle body 140. Additionally, the proximal end 245 of the handle push rod 155 is disposed within the internal cavity 175, and from there the handle push rod 155 extends distally within the longitudinal channel 200 of the tubular shaft 145. As further shown, the handle push rod 155 is sized such that its distal end 250, including the distal mating feature 255, can extend distally beyond the distal end 198 of the tubular shaft 145.

In various embodiments, the plunger 150 and the handle push rod 155 are slidably and rotatably coupled to the handle body 140 and retained partially within the internal cavity 175 and the longitudinal channel 200, as shown in FIGS. 2A and 2B. Thus, the plunger 150 and the handle push rod 155 can be advanced distally and retracted proximally with respect to the handle body 140 under clinician control, to effect deployment of the tissue fixation apparatus 115 (see FIG. 1A). As further shown, in the illustrated embodiment, the guide pin 158 is spring-biased toward the plunger 150 under the operation of the spring 160, and extends partially into the groove arrangement 230 of the plunger 150. In this manner, the guide pin 158 operates to regulate and delimit longitudinal and rotational movement of the plunger 150 and the handle push rod 155 relative to the handle body 140. In addition, prior to deployment of the tissue fixation apparatus 115, in one embodiment, the tab 134 on the tension line 132 of the tissue fixation apparatus 115 can be releasably coupled to the intermediate section 220 of the plunger 150 between the knob 235 and the handle body 140 (see FIG. 1A). In this arrangement, the tab 134 also operates to prevent unintended advancement of the plunger 150 relative to the handle body 140, thus requiring the tab 134 to be removed from the plunger 150 prior to deployment of the first tissue anchor of the fixation apparatus 115. In other embodiments, other or additional means can be employed to regulate the movement of the plunger 150 and the handle push rod 155 relative to the handle body 140.

Figure 3:
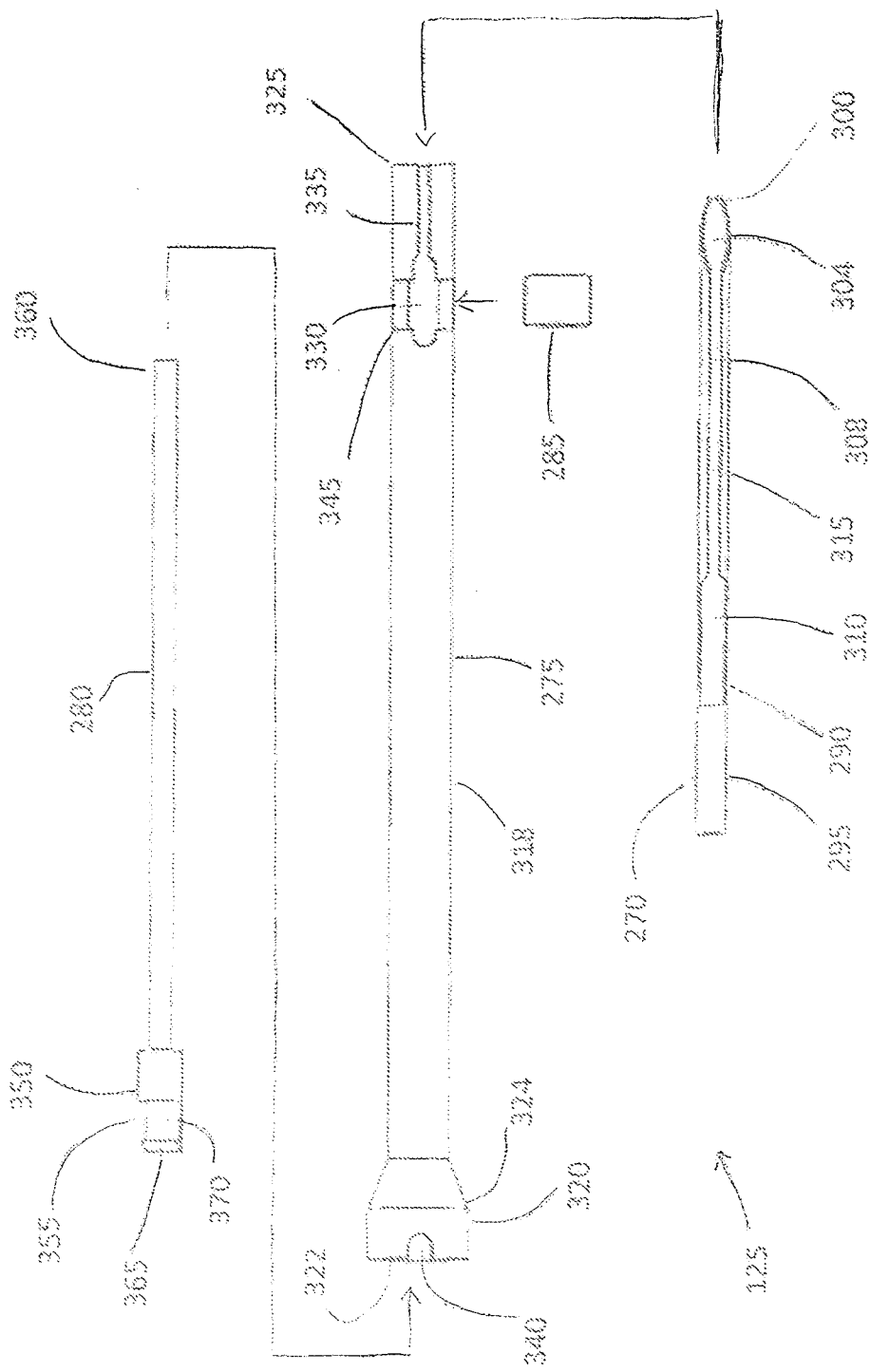
FIG. 3 is an exploded view of a needle cartridge portion of the delivery tool of the tissue fixation system of FIG. 1 according to one embodiment.
Figure 4:
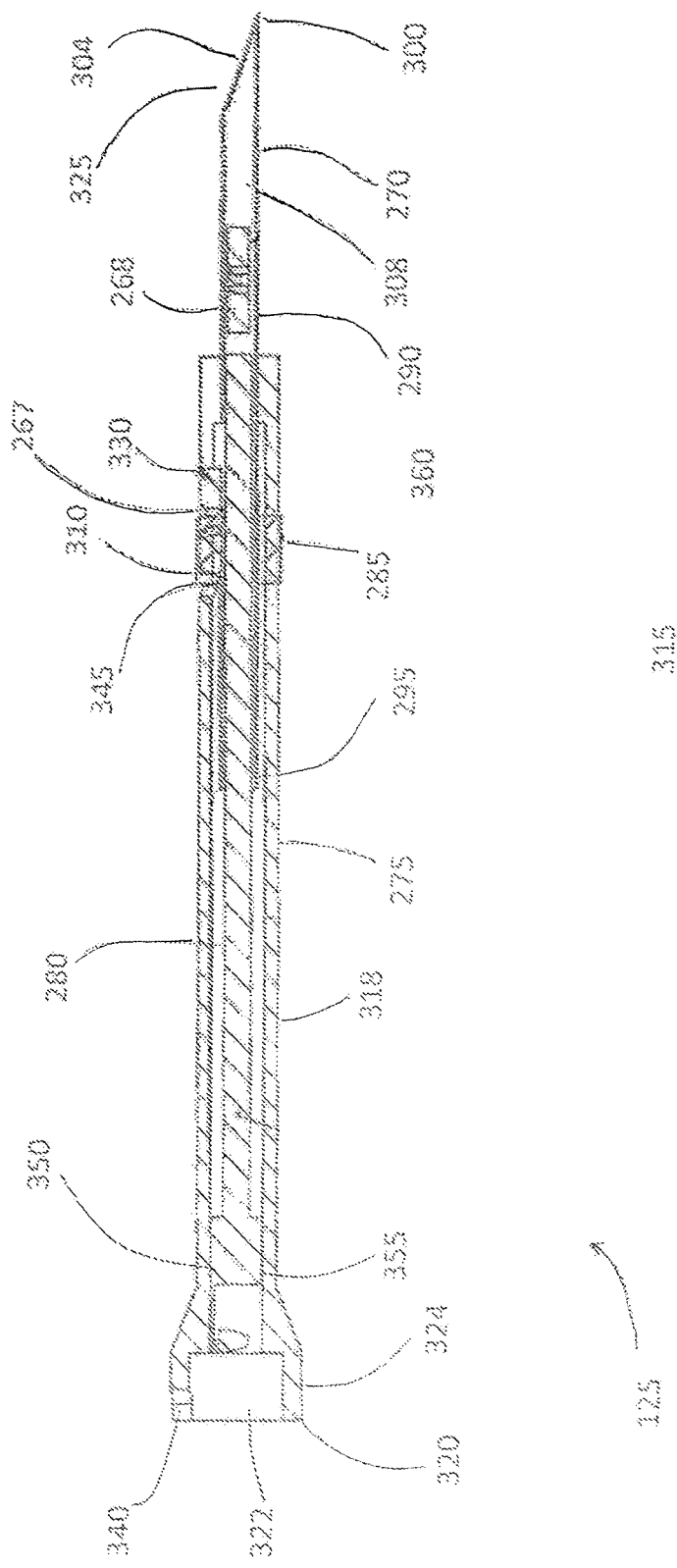
FIG. 4 is a cross-sectional elevation views of the needle cartridge portion of the delivery tool of the tissue fixation system of FIG. 1 according to one embodiment.

FIG. 3 is an exploded view of a needle cartridge assembly 125 of the delivery tool 110, and FIG. 4 is a cross-sectional elevation views of the needle cartridge assembly 125 according to one embodiment. In FIG. 4, tissue anchors 267, 268 of the fixation apparatus 115 are shown for illustration purposes. As shown, the needle cartridge assembly 125 includes a needle cannula 270, a tubular sleeve 275, a cartridge push rod 280 and a resilient band 285. As further shown, the needle cannula 270 has an outer wall 290 that defines a proximal portion 295, an opposite sharpened distal tip 300 having a distal opening 304, and an internal chamber 308. Additionally, in the illustrated embodiment, the needle cannula 270 includes a needle side opening 310 and a slot 315. As shown, both the needle side opening 310 and the slot 315 extend through the outer wall 290 to the internal chamber 308, with the slot 315 extending from the distal opening 304 proximally to the side opening 310.

As further shown, the tubular sleeve 275 includes an outer wall 318 defining a proximal end 320 having a proximal opening 322, a proximal head 324, and an opposite distal end 325. Additionally, in the illustrated embodiment, the tubular sleeve 275 includes a sleeve side opening 330, a slot 335, a proximal alignment notch 340 and a circumferential recess 345. As shown, in one embodiment, the sleeve side opening 330 and the slot 335 extend through the outer wall 318, with the slot 335 extending from the distal end 325 to the sleeve side opening 330. Additionally, the proximal alignment notch 340 extends longitudinally from the proximal end 320.

In the illustrated embodiment, the cartridge push rod 280 includes a proximal end 350 having a proximal mating feature 355, and an opposite distal end 360. As further shown, the proximal mating feature 355 includes an inwardly projecting tooth 365 and a generally flat face 370 extending distally with respect to the tooth 365. In various embodiments, the cartridge push rod 280 can be configured in substantially the same or an identical manner as the handle push rod 155 discussed previously.

As can be seen in FIGS. 3 and 4, when assembled, the proximal portion 295 of the needle cannula 270 is disposed within and fixedly coupled to the tubular sleeve 275, and is positioned such that the needle side opening 310 is axially and radially aligned with the sleeve side opening 330, and also such that the needle slot 315 is axially and radially aligned with the sleeve slot 335. The side openings 310, 335 are sized to receive the tissue anchors 267, 268 therethrough with the tissue anchors 267, 268 generally aligned with the longitudinal axis of the needle cannula 270 and tubular sleeve 275. Additionally, the slots 315, 335 are sized to have widths smaller than the widths of the tissue anchors 267, 268 so as to prevent the tissue anchors 267, 268 from exiting the chamber 308 of the needle cannula 270 during their deployment. In various embodiments, the slots 315, 335 operate to provide a means by which a portion of the suture assembly of the tissue fixation apparatus 115 (see FIG. 1) can exit the internal chamber 308 when one of the tissue anchors 267, 268, to which the suture assembly is coupled, is disposed in the internal chamber 308.

As further shown, the distal end 360 of the needle push rod 280 is slidably disposed within the internal chamber 308 of the needle cannula 270, and the proximal end 350 is disposed within the tubular sleeve 275 within the proximal portion 295 thereof. As shown, the proximal mating feature 355 has an outer dimension slightly smaller than the inner dimension of the tubular sleeve 275, thus allowing translation and rotation of the cartridge push rod 280 while minimizing clearance between the mating feature 355 and the tubular sleeve 275 wall.

In various embodiments, the proximal head 324 and the proximal opening 322 of the tubular sleeve 275 are sized and configured to receive the distal end 198 of the tubular shaft 145 of the handle mechanism 120. Thus, to couple the handle mechanism 120 and the needle cartridge assembly 125 together, the distal end 198 of the tubular shaft 145 is inserted into the proximal opening 322 of the tubular sleeve 275. In one embodiment, the distal end 198 of the tubular shaft 145 and the proximal opening 322 of the tubular sleeve 275 are sized to form an interference fit therebetween to couple the handle mechanism 120 to the needle cartridge assembly 125. In other embodiments, other means (e.g., ball/socket joints, snap-fit connections, etc.) can be utilized to releasably couple the handle mechanism 125 and the needle cartridge assembly 125. The alignment pin 205 on the tubular shaft 145 can be received in the notch 340 in the tubular sleeve during the insertion of the distal end 198 into the tubular sleeve 275 to radially align the tubular shaft 145 and the tubular sleeve 275.

The mating features 255, 355 on the push rods 155, 280 are configured to engage one another upon coupling the handle mechanism 120 and the needle cartridge assembly 125. In the one embodiment, as the handle mechanism 120 and the needle cartridge assembly 125 are joined together, the teeth 260, 365 are configured to slide over one another to position the tooth 260 on the handle push rod 155 is adjacent to the flat face 370 on the cartridge push rod 280, while the tooth 365 is positioned adjacent to the flat face 265 of the handle push rod 155. This arrangement links the push rods 155, 280 together such that push rods 155, 280 can be advanced distally and retracted proximally together upon operator control of the plunger 150, with the teeth 260, 365 inhibiting unintended axial separation of the push rods 155, 280. At the same time, the illustrated coupling arrangement still allows the mating features 255, 355 to disengage one another when the needle cartridge assembly 125 is intentionally separated from the handle mechanism 125 by the clinician. In various other embodiments, other means (e.g., ball/socket joints, snap-fit connections, etc.) can be employed to releasably couple the push rods 155, 280.

In one embodiment, the push rods 155, 280 can be automatically coupled together in the above manner upon insertion of the distal end 198 of the tubular shaft 145 into the proximal opening 322 of the tubular sleeve 275. In other embodiments, the push rods 155, 280 can be coupled together as a subsequent assembly step (e.g., by advancing the plunger 150 a predetermined distance after fully inserting the distal end 198 of the tubular shaft 145 into the proximal opening 322 of the tubular sleeve 275.

In various embodiments, where the tissue fixation apparatus 115 is pre-loaded onto the needle cartridge assembly 125, once the needle cartridge assembly 125 is coupled to the handle mechanism 120, the tab 134 can be coupled to the intermediate section 220 of the plunger 150 between the control knob 235 and the proximal end 165 of the handle body 140, as shown in FIG. 1A.

FIG. 4 illustrates, in cross-section, the needle cartridge assembly 125 with the tissue anchors 267, 268 loaded in a pre-deployment configuration. As shown, in this configuration, the tissue anchor 267 is positioned within the internal chamber 308 of the needle cannula 270, and the tissue anchor 268 is positioned within the side openings 310, 330 of the needle cannula 270 and the tubular sleeve 275, respectively. The suture assembly 130 of the tissue fixation apparatus 115 (see FIG. 1) is omitted for in FIG. 4, although those skilled in the art will readily appreciate that the suture assembly 130 would be present in an assembled kit including the needle cartridge assembly 125 and the pre-loaded tissue fixation apparatus 130. As further shown, the resilient band 285 is positioned around the tubular sleeve 270 over the side opening 330, and thus over the tissue anchor 268, thus urging the tissue anchor 268 radially inward toward the chamber 308 of the needle cannula 270. However, as shown, in the pre-deployment configuration, the cartridge push rod 280 is positioned adjacent to the side openings 310, 330 so as to prevent the tissue anchor 268 from being pushed into the internal chamber 308 by the resilient band 285.

In various embodiments, the plunger 150 and the handle and cartridge push rods 155, 280 are configured to operate between at least one extended position and at least one retracted position relative to the handle body 140 and the needle cannula 270 to effect loading, retention, and deployment of the tissue anchors 267, 268 into and from the chamber 308 of the needle cannula 270. That is, the plunger 150 and the handle and cartridge push rods 155, 280 can be further extended distally from the position shown in FIG. 4, thereby ejecting the tissue anchor 267 from the distal opening 304 of the needle cannula 270 while still preventing the tissue anchor 268 from entering the chamber 308. The plunger 150 and the handle and cartridge push rods 155, 280 are further configured so as to be subsequently retractable to a retracted position in which the distal end 360 of the cartridge push rod 280 is positioned proximal to the side openings 310, 330. In this position (not shown in FIG. 4), the tissue anchor 268 can be pushed into the internal chamber 308 under the operation of a radial force exerted on the tissue anchor 268 by the band 285. The plunger 150 and the handle and cartridge push rods 155, 280 can then be again extended to an extended position to eject the tissue anchor 268 from the distal opening 304 of the needle cannula 270. Subsequently, the needle cartridge assembly 125 can be disconnected from the handle mechanism 120 and discarded and, if the clinician desires or if necessary for the particular procedure, a second needle cartridge assembly 125 with a tissue fixation apparatus 115 loaded thereon can be connected to the handle mechanism 120 and the above steps repeated as required.

In various embodiments, the tissue fixation system 100 can be provided in a disassembled state, including the handle mechanism 120, and one or more kits each including the needle cartridge assembly 125 pre-loaded with the tissue fixation apparatus 115. In some embodiments, different ones of the needle cartridge assembly 125/tissue fixation apparatus 115 kits can have different configurations (e.g., different sizes, lengths, anchor and/or suture configurations, etc.) so as to provide a wide range of flexibility and accommodate a range of clinical needs. In such embodiments, the clinician can select the kit(s) having the particular needle cartridge assembly 125 and/or tissue fixation apparatus 115 configuration(s) best suited for the particular procedure being performed.

Figure 5A:
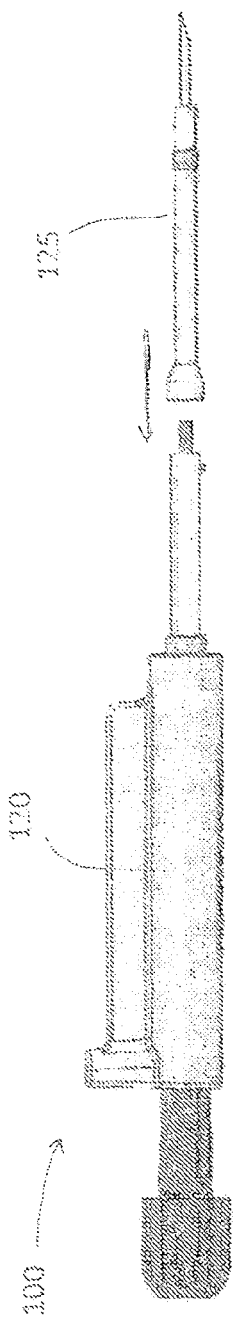
FIGS. 5A-5F are elevation views of the tissue fixation system of FIG. 1 shown in sequential stages of operation.
Figure 5B:
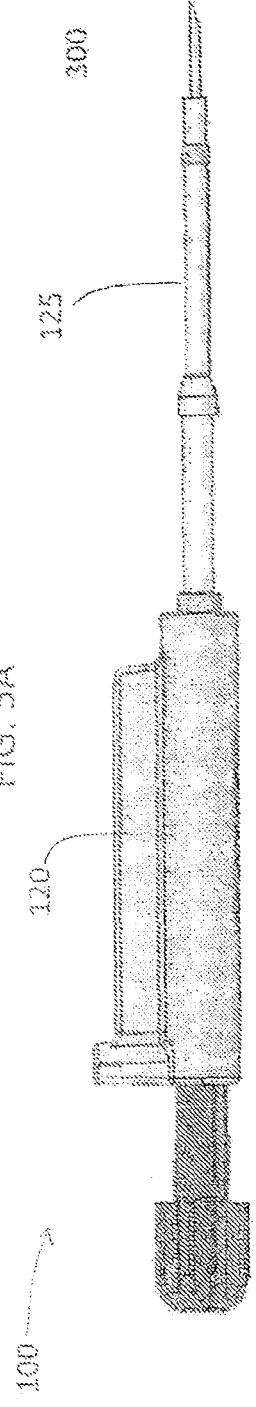

FIGS. 5A-5F are elevation views of the tissue fixation system 100 in sequential stages of operation. FIG. 5A illustrates the handle mechanism 120 and the needle cartridge assembly 125 prior to being connected together. For ease of illustration, the suture assembly 130 of the tissue fixation apparatus 115 (see FIG. 1A) has been omitted from FIGS. 5A-5F, although one skilled in the art will readily recognize the presence of these elements in the various embodiments. The handle mechanism 120 and the needle cartridge assembly 125 are then joined together, e.g., in the manner described above, for form the assembled tissue fixation system 100, as shown in FIG. 5B.

Figure 5C:
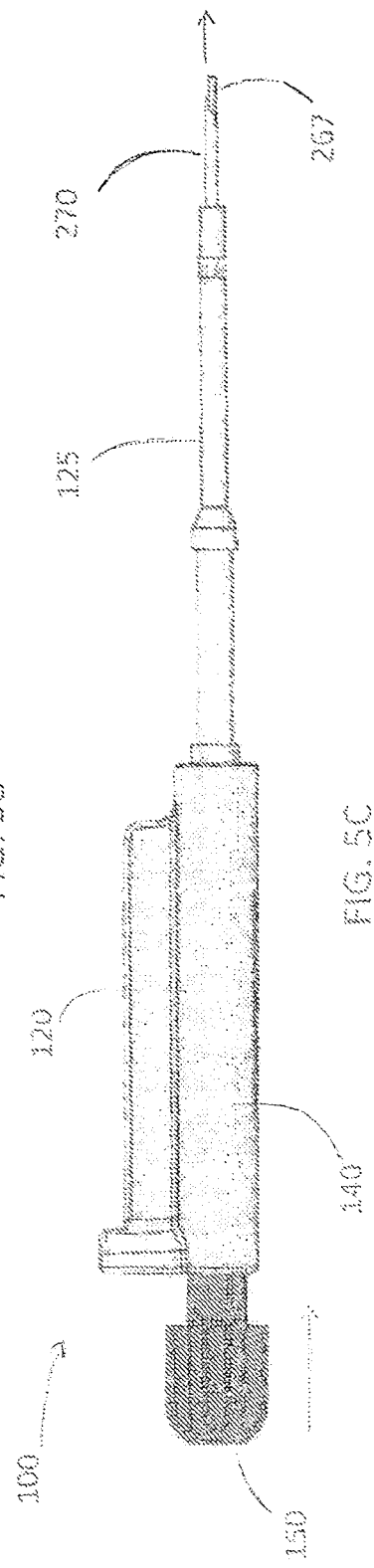

Subsequently, the distal tip 300 can be inserted into the target tissue location a desired depth, depending on the particular procedure being performed. For example, when used in an orthopedic procedure such as a disc annulus re-approximation or a meniscal repair procedure, the distal tip 300 can be inserted into or through the outer surface of the annulus or meniscus proximate the defect to be re-approximated. As another example, when used to secure an implant to soft tissue, the distal tip can be inserted into the soft tissue adjacent to the implant at a first location. Once the distal tip 300 is inserted as desired, the plunger 150 can be advance distally relative to the handle body 140, thus ejecting the first tissue anchor 267 from the needle cannula 270 and into the target tissue, as shown in FIG. 5C.

Figure 5D:
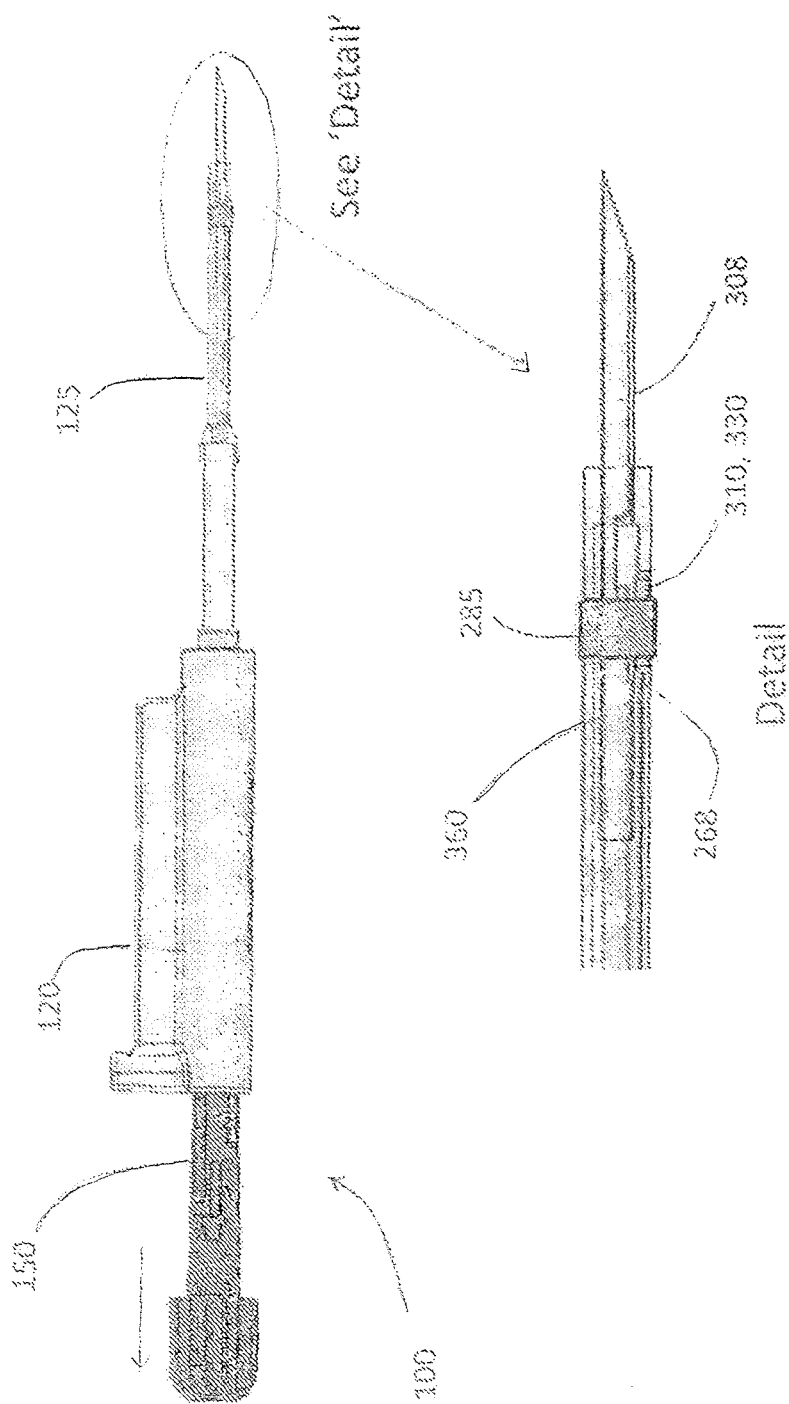

Next, the distal tip 300 can be removed from the target tissue at the first location and relocated to a second location selected as required for the particular procedure (e.g., either on the other side of the defect in the annulus or knee meniscus, or on the other side of the implant to be secured). The distal tip 300 can then be inserted into the tissue at this second location. Subsequently, the plunger 150, and consequently, push rods 155, 280 can be retracted proximally so that the distal end 360 of the push rod 280 is positioned proximal to the side openings 310, 330, as shown in FIG. 5D, and the corresponding "Detail." With the push rods 155, 280 so positioned, the tissue anchor 268 is loaded into the internal chamber 308 under the action of the band 285, as shown. In one embodiment, the plunger 150, and in particular, the groove arrangement 230, is configured such that it must be rotated to a free position to allow for retraction of the plunger 150 and the push rods 155, 280, although in other embodiments other plunger movement regulation techniques are utilized.

Figure 5E:
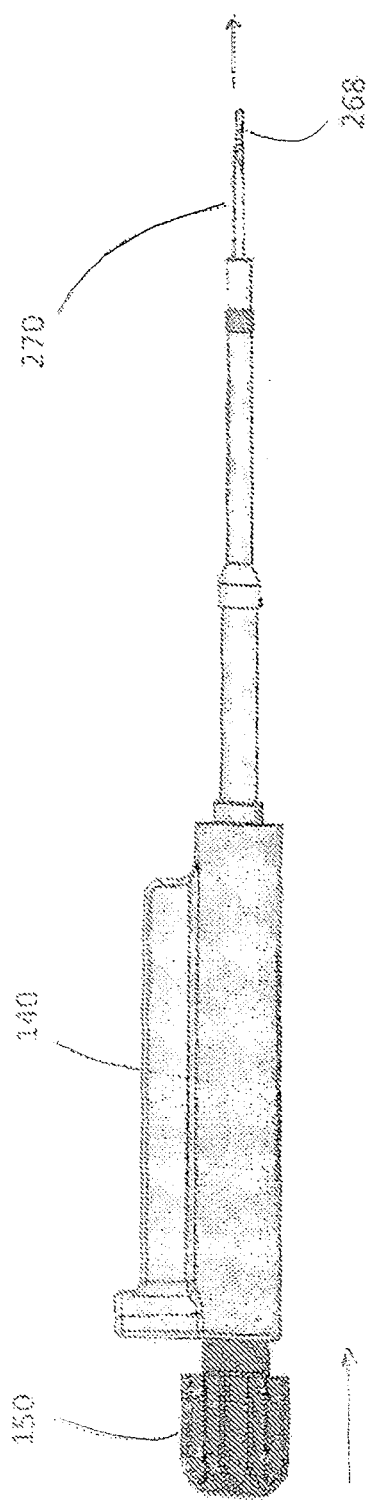
Figure 5F:
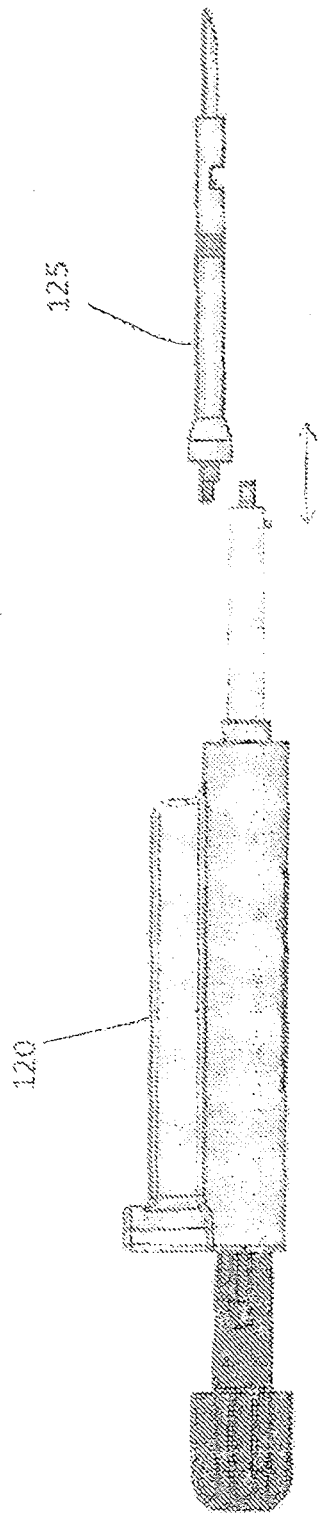

Next, the plunger 150 and the push rods 155, 280 can again be extended distally relative to the handle body 140, thus ejecting the second tissue anchor 268 from the needle cannula 270 and into the target tissue, as shown in FIG. 5E. The distal tip 300 can then be removed from the tissue. As shown in FIG. 5F, the handle mechanism 120 and the needle cartridge assembly 125 can be disconnected from one another. If desired, a second needle cartridge assembly 125 and tissue fixation apparatus 115 can then be connected to the same handle mechanism 120 for deployment as dictated by the particular procedure being performed.

The materials used in the delivery tool 110 can include any number of biocompatible materials having suitable mechanical properties. Exemplary materials can include, but are not limited to: metals, such as stainless steels, nickel, titanium alloy, and titanium; plastics, such as polytetrafluoroethylene (PTFE), polypropylene, polyether etherketone (PEEK™), polyethylene, polyethylene teraphthalate (PET) and polyurethane, acrylic, polycarbonate, engineering plastics; and/or composites. In short, any suitable materials, whether now known or later developed, can be utilized to construct the implant delivery tool 110 within the scope of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed as new and desired to be protected under Letters Patent of the United States is:

1. A device for deploying tissue anchors, the device comprising:
    a handle defining an internal cavity;
    a tubular assembly extending distally from the handle and comprising a groove and a first side opening;
    a needle cannula comprising an outer wall, a proximal portion disposed within the tubular assembly, an opposite sharpened distal tip having a distal opening, an internal chamber extending from the proximal portion through the distal opening, and a second side opening through the outer wall;
    a plunger assembly slidably coupled to the handle and comprising a proximal end positioned external to and proximal to the handle and a push rod assembly, wherein portions of the plunger assembly are slidably disposed within the handle, the tubular assembly, and the needle cannula; and
    a resilient band disposed about the tubular assembly within the groove and over the first side opening:
    wherein the device is configured and arranged so that, prior to deployment, a first tissue anchor can be disposed within the internal chamber of the needle cannula and a second tissue anchor can be disposed external to the internal chamber within the first side opening in the tubular assembly, and wherein the plunger assembly is positioned to prevent the second tissue anchor from entering the internal chamber while the resilient band operates to urge the second tissue anchor toward the internal chamber.

2. The device of claim 1, further comprising the first tissue anchor disposed within the internal chamber of the needle cannula; and
    the second tissue anchor disposed external to the internal chamber within the first side opening in the tubular assembly.

3. The device of claim 2, further comprising an adjustable suture assembly coupled to the first anchor and the second anchor.

4. The device of claim 3, wherein the device is configured and arranged for the adjustable suture assembly to be releasably coupleable to the handle.

5. A method of using the device of claim 2, the method comprising:
    inserting the sharpened distal tip of the needle cannula into patient tissue at a first location;
    advancing the plunger assembly to eject the first tissue anchor from the needle cannula into the patient tissue at the first location;
    withdrawing the needle cannula from the first location;
    inserting the sharpened distal tip into the patient tissue at a second location;
    retracting the plunger assembly with respect to the needle cannula to allow the second tissue anchor to be pushed into the interior chamber of the needle cannula under the operation of the resilient band disposed about the needle cannula and the second tissue anchor;
    advancing the plunger assembly to eject the second tissue anchor from the needle cannula into the patient tissue at the second location; and
    withdrawing the needle cannula from the patient tissue.

6. The method of claim 5, wherein the device further comprises an adjustable suture assembly coupled to the first anchor and the second anchor, the method further comprising tightening the adjustable suture assembly.

7. The device of claim 1, wherein the plunger assembly comprises a plunger slidably coupled to the handle and comprising a proximal end of the handle and a distal end positioned within the internal cavity of the handle.

8. The device of claim 7, wherein the plunger assembly comprises
- a first push rod extending distally from the plunger and slidably disposed within the tubular assembly, the first push rod comprising a distal mating feature; and
- a second push rod slidably disposed within the internal chamber of the needle cannula and comprising a proximal mating feature configured to engage the distal mating feature of the first push rod.

9. The device of claim 8, wherein the distal mating feature of the first push rod is releasably coupleable to the proximal mating feature of the second push rod.

10. The device of claim 1 wherein the tubular assembly comprises
- a tubular shaft extending distally from the handle and comprising a distal end: and
- a tubular sleeve disposed about a portion of the needle cannula and comprising a proximal end, the groove, and the first side opening, the proximal end of the tubular sleeve configured to mate with the distal end of the tubular shaft.

11. The device of claim 10, wherein the distal end of the tubular shaft is configured and arranged to releasably mate with the proximal end of the tubular sleeve.

12. The device of claim 1, wherein the plunger assembly is configured and arranged to operate between an extended position and a retracted position wherein in the extended position the plunger assembly extends to eject the first tissue anchor from the internal chamber through the distal opening of the needle cannula while preventing the second tissue anchor from entering the internal chamber, wherein in the retracted position the plunger assembly is retracted to allow the second tissue anchor to be urged into the internal chamber through the first side opening and the second side opening by the resilient band.

13. The device of claim 1, wherein the plunger assembly comprises an intermediate section including an outer surface and a groove arrangement therein, wherein the handle comprises a guide pin extending radially inward, the guide pin being spring biased toward the plunger assembly so as to extend partially within the groove arrangement to regulate longitudinal movement of the plunger assembly relative to the handle.

14. A device for deploying a tissue fixation apparatus, the device comprising:
- a handle defining an internal cavity;
- a tubular shaft extending distally from the handle;
- a plunger slidably coupled to the handle and comprising a proximal end positioned external to the handle and a distal end positioned within the internal cavity of the handle;
- a handle push rod extending from the distal end of the plunger and slidably disposed within the tubular shaft;
- a needle cannula comprising an outer wall, a proximal portion, an opposite sharpened distal tip having a distal opening, an internal chamber extending from the proximal portion through the distal opening, and a needle side opening through the outer wall;
- a tubular sleeve disposed about a portion of the needle cannula and releasably mateable with the tubular shaft, the tubular sleeve comprising a groove and a sleeve side opening;
- a cartridge push rod slidably disposed within the internal chamber of the needle cannula and releasably mateable with the handle push rod; and
- a resilient band disposed about the tubular sleeve within the groove and over the sleeve side opening;
- wherein the device is configured and arranged to receive a first tissue anchor within the internal chamber of the needle cannula and a second tissue anchor within the side sleeve opening and external to the internal chamber of the needle cannula.

15. The device of claim 14, further comprising the first tissue anchor disposed within the internal chamber of the needle cannula; and
- the second tissue anchor disposed external to the internal chamber within the sleeve side opening in the tubular sleeve.

16. The device of claim 15, further comprising an adjustable suture assembly coupled to the first anchor and the second anchor.

17. The device of claim 16, wherein the device is configured and arranged for the adjustable suture assembly to be releasably coupleable to the handle.

18. A method of using the device of claim 15, the method comprising:
- inserting the sharpened distal tip of the needle cannula into patient tissue at a first location;
- advancing the cartridge push rod within the needle cannula to eject the first tissue anchor from the needle cannula into the patient tissue at the first location;
- withdrawing the needle cannula from the first location;
- inserting the sharpened distal tip into the patient tissue at a second location;
- retracting the cartridge push rod with respect to the needle cannula to allow the second tissue anchor to be pushed into the interior chamber of the needle cannula under the operation of the resilient band disposed about the needle cannula and the second tissue anchor;
- advancing the cartridge push rod within the needle cannula to eject the second tissue anchor from the needle cannula into the patient tissue at the second location; and
- withdrawing the needle cannula from the patient tissue.

19. The method of claim 18, wherein the device further comprises an adjustable suture assembly coupled to the first anchor and the second anchor, the method further comprising tightening the adjustable suture assembly.

20. The device of claim 14, wherein the plunger and the handle push rod and the cartridge push rod are configured to operate between an extended position and a retracted position, wherein in the extended position the cartridge push rod is configured and arranged to eject the first tissue anchor from the internal chamber through the distal opening of the needle cannula while preventing the second tissue anchor from entering the internal chamber, wherein in the retracted position the cartridge push rod is positioned proximal to the sleeve side opening so as to allow the second tissue anchor to be urged into the internal chamber through the needle side opening by the resilient band.

* * * * *